United States Patent
Huang et al.

(10) Patent No.: US 8,357,509 B2
(45) Date of Patent: Jan. 22, 2013

(54) MICROBIAL EXPRESSION OF TOBACCO OSMOTIN FOR BIOCIDAL AND MEDICAL APPLICATIONS

(75) Inventors: Tung-Shi Huang, Auburn, AL (US);
Ywh-Min Tzou, Auburn, AL (US);
Narendra Slngh, Auburn, AL (US);
Bryan A. Chin, Auburn, AL (US)

(73) Assignee: Auburn University, Auburn, AL (US)

( * ) Notice: Subject to any disclaimer, the term of this patent is extended or adjusted under 35 U.S.C. 154(b) by 53 days.

(21) Appl. No.: 12/972,115

(22) Filed: Dec. 17, 2010

(65) Prior Publication Data

US 2011/0318782 A1 Dec. 29, 2011

Related U.S. Application Data

(60) Provisional application No. 61/287,583, filed on Dec. 17, 2009.

(51) Int. Cl.
*C12P 1/00* (2006.01)
*C12P 21/06* (2006.01)
*C12P 21/04* (2006.01)
*C07K 00/01* (2006.01)
*A61K 36/00* (2006.01)

(52) U.S. Cl. ........ 435/41; 435/69.1; 435/71.1; 530/350; 530/379

(58) Field of Classification Search ........................ None
See application file for complete search history.

(56) References Cited

U.S. PATENT DOCUMENTS 7,396,664 B2 7/2008 Daly et al.
2007/0202126 A1* 8/2007 Joerger et al. ............. 424/195.17
2008/0318855 A1* 12/2008 Chen et al. ..................... 514/12

OTHER PUBLICATIONS de A Campos et al., Expression in *Escherichia coli*, purification, refolding and antifungal activity of an osmotin from *Solanum nigrum*; Microbial Cell Factories, vol. 7 No. 7, pp. 1-10, 2008.*
Singh et al., Molecular Cloning of Osmotin and Regulation of Its Expression by ABA and Adaptation to Low Water Potential; Plant Physiology, vol. 90, pp. 1096-2101, 1989.*
Yun et al., Stress proteins on the yeast cell surface determine resistance to osmotin, a plant antifungal protein; PNAS vol. 94, pp. 7082-7087.*
Baneyx, Recombinant protein expression in *Escherichia coli*; Curr Opin Biotechnoloy, vol. 10, 411-421, 1999.*
Singh et al., Molecular Cloning of Osmotin and Regulation of Its Expression by ABA and Adaptation to Low Water Potential; Plant Physiology, vol. 90, pp. 1096-2101, 1989—Medline record dated Apr. 1993 showing osmotin gene sequence.*
Cregg et al., Recombinant Protein Expression in *Pichia pastoris*; Molecular Biotechnology, vol. 16, pp. 23-52, 2000.*
Abad et al., "Antifungal activity of tobacco osmotin has specificity and involves plasma membrane permeabilization", Plant Science, 1996, 118:11-23.

Altschul et al., "Basic Local Alignment Search Tool", J. Mol. Biol., 1990, 215:403-410.
Campos et al., "Expression in *Escherichia coli*, purification, refolding and antifungal activity of an osmotin from *Solanum nigrum*", Microbial Cell Factories, 2008, 7(7):1-10.
Hermes-Lima et al., "The iron chelator pyridoxal isonicotinoyl hydrazone (PIH) and its analogues prevent damage to 2-deoxyribose mediated by ferric iron plus ascorbate", Biochimica et Biophysica Acta, 2000, 1523:154-160.
Kononowicz et al., "Regulation of the Osmotin Gene Promoter", The Plant Cell, May 1992, 4:513-524.
Liu et al., "Osmotin overexpression in potato delays development of disease symptoms", Proc. Natl. Acad. Sci. USA, Mar. 1994, 91:1888-1892.
Min et al., "Crystal Structure of Osmotin, a Plant Antifungal Protein", Proteins: Structure, Function, and Bioinformatics, 2004, 54:170-173.
Narasimhan et al., "A Plant Defense Response Effector Induces Microbial Apoptosis", Molecular Cell, Oct. 2001, 8:921-930.
Narasimhan et al., "Overexpression of a cell wall glycoprotein in *Fusarium oxysporum* increases virulence and resistance to a plant PR-5 protein", The Plant Journal, 2003, 36:390-400.
Narasimhan et al., "Osmotin is a homoog of mammalian adiponectin and controls apoptosis in yeast through a homolog of mammalian adiponectin receptor", Molecular Cell, Jan. 21, 2005, 17:171-180.
Rahbarizadeh et al., "Over expression of anti-MUC1 single-domain antibody fragments in the yeast *Pichia pastoris*", Molecular Immunology, 2006, 43:426-435.
Singh et al., "Proteins Associated with Adaptation of Cultured Tobacco Cells to NaCl", Plant Physiol., 1985, 79:126-137.
Singh et al., "Characterization of Osmotin", Plant Physiol., 1987, 85:529-536.
Singh et al., "Molecular Cloning of Osmotin and Regulation of Its Expression of ABA and Adaptation to Low Water Potential", Plan Physiol., 1989, 90:1096-1101.
Studier et al., "Protein Production by Auto-Induction in High-Density Shaking Cultures", Protein Expr Purif., May 2005, 41(1):207-234.
Tatusova et al., "BLAST 2 Sequences, a new tool for comparing protein and nucleotide sequences", FEMS Microbiology Letters, 1999, 174:247-250.
Woloshuk et al., "Pathogen-Induced Proteins with Inhibitory Activity toward *Phytophthora infestans*", The Plant Cell, Jun. 1991, 3:619-628.
Yun et al., "Stress proteins on the yeast cell surface determine resistance to osmotin, a plant antifungal protein", Proc Natl Acad Sci, Jun. 1997, 94:7082-7087.
Yun et al., "Osmotin, a Plant Antifungal Protein, Subverts Signal Transduction to Enhance Fungal Cell Susceptibility", Molecular Cell, May 1998, 1:807-817.

(Continued)

*Primary Examiner* — Celine Qian
*Assistant Examiner* — Addison D Ault
(74) *Attorney, Agent, or Firm* — Andrus, Sceales, Starke & Sawall, LLP (57) ABSTRACT

Disclosed herein are recombinant tobacco osmotin polypeptides and methods for expressing tobacco osmotin polypeptides in microbial host cells. The recombinant tobacco osmotin polypeptides produced by the methods disclosed herein may be utilized as biocides or as therapeutic agents in medicaments.

15 Claims, 2 Drawing Sheets

OTHER PUBLICATIONS

Fernandez et al., "The determination of ferric iron in plants by HPLC using the microbial iron chelator desferrioxamine E", BioMetals, 2005, 18:53-62.

Giri, "Chromatofocusing", Methods in Enzymology, 1990, 182:380-392.

Gorbunoff, "Protein Chromatography on Hydroxyapatite Columns", Methods in Enzymology, 1990, 182:329-339.

Guida et al., "Aluminum toxicity and binding to *Escherichia coli*", Arch Microbiol, 1991, 156:507-512.

Guo et al., "Molecular cloning of the cDNA encoding laccase from *Trametes versicolor* and heterologous expression in *Pichia methanolica*", Appl. Microbiol. Biotechnol., 2005, 69:178-183.

Hiep et al., "Transformation in the Methylotrophic Yeast *Pichia methanolica* utilizing Homologous ADE1 and Heterologous *Saccharomyces cerevisiae* ADE2 and LEU2 Genes as Genetic Markers", Yeast, 1993, 9:1189-1197.

Hiep et al., "Yeast Sequencing Reports", Yeast, 1993, 9:1251-1258.

Hu et al., "Codon optimization, expression, and characterization of an internalizing anti-ErbB2 single-chain antibody in *Pichia pastoris*", Protein Expression and Purification, 2006, 47:249-257.

Kennedy et al., "Hydrophobic Chromatography", Methods in Enzymology, 1990, 182:339-343.

Liu et al., "In vivo and in vitro activity of trancated osmotic that is secreted into the extracellular matrix", Plant Science, 1996, 121:123-131.

Melchers et al., "Extracellular targeting of the vacuolar tobacco proteins AP24, chitinase and β-1,3-glucanase in transgenic plants", Plant Molecular Biology, 1993, 21:583-593.

Ostrove, "Affinity Chromatography: General Methods", Methods in Enzymology, 1990, 182:357-371.

Ostrove et al., "Affinity Chromotography: Specialized Techniques", Methods in Enzymology, 1990, 182:371-379.

Rossomando, "Ion-exchange chromotography", Methods in Enzymology, 1990, 182:309-317.

Slininger et al., "Nitrogen source and mineral optimization enhance d-xylose conversion to ethanol by the yeast *Pichia stipitis* NRRI Y-7124", Appl. Microbiol. Biotechnol., 2006, 72:1285-1296.

Stellwagen, "Gel Filtration", Methods in Enzymology, 1990, 182:317-328.

Stellwagen, "Chromatography on Immobilized Reactive Dyes", Methods in Enzymology, 1990, 182:343-357.

Stintzi et al., "Identification of a basic pathogenesis-related, thaumatin-like protein of virus-infected tobacco as osmotin", Physiological and Molecular Plant Pathology, 1991, 38:137-146.

Tzou et al., "Expression of truncated tobacco osmotin in *Escherichia coli*: purification and antifungal activity", Biotechnol Lett, 2011, 33:539-543.

Vigers et al., "Thaumatin-like pathogenesis-related proteins are antifungal", Plant Science, 1992, 83:155-161.

Zhao et al., "Increasing the cell viability and heterologous protein expression of *Pichia pastoris* mutant deficient in PMR1 gene by culture condition optimization", Appl Microbiol Biotechnol, 2008, 81:235-241.

\* cited by examiner

FIG. 1

```
                            1                10                20               30               40                 57
SnOLP        (SEQ ID NO:8)  (1)  MGYSRSSFVFFLLTFVTYTYATSFEVRNNCPYTVWAASTPIGGGRRLDRGQTWVINA
TOBOSM3d     (SEQ ID NO:7)  (1)  ---------------------ATIEVRNNCPYTVWAASTPIGGGRRLDRGQTWVINA
Consensus    (SEQ ID NO:9)  (1)                      S-EVRNNCPYTVWAASTPIGGGRRLDRGQTWVINA 58      +       70         +      80               90              100         -      114
SnOLP                      (58)  PRGTSMARIWGRTNCNFDGAGRGSCQTGDCGGVLQCTGWGKPPNTLAEYALNQFSNL
TOBOSM3d                   (37)  PRGTKMARVWGRTNCNFNAAGRGTCQTGDCGGVLQCTGWGKPPNTLAEYALDQFSGL
Consensus                  (58)  PRGT-MARIWGRTNCNF-AAGRGSCQTGDCGGVLQCTGWGKPPNTLAEYAL-QFS-L 115            120              130              140              150         +-     171
SnOLP                     (115)  DFWDISLVDGFNIPMTFAPTNPSGGKCHSIQCTANINGECPAALRVPGGCNNPCTTF
TOBOSM3d                   (94)  DFWDISLVDGFNIPMTFAPTNPSGGKCHAIHCTANINGECPRELRVPGGCNNPCTTF
Consensus                 (115)  DFWDISLVDGFNIPMTFAPTNPSGGKCHAI-CTANINGECP--LRVPGGCNNPCTTF 172            180         +    190              200              210         +      228
SnOLP                     (172)  GGQYCCTQGPCGPTELSKFFKQRCPDAYSYPQDDPTSTFTCPSDSTNYRVVFCPNG
TOBOSM3d                  (151)  GGQQYCCTQGPCGPTFFSKFFKQRCPDAYSYPQDDPTSTFTCPGGSTNYRVIFCP--
Consensus                 (172)  GGQQYCCTQGPCGPT--SKFFKQRCPDAYSYPQDDPTSTFTCP--STNYRVIFCP
```

FIG. 2

SEQUENCE LISTING

<160> NUMBER OF SEQ ID NOS: 9

<210> SEQ ID NO 1
<211> LENGTH: 732
<212> TYPE: DNA
<213> ORGANISM: Nicotiana tabacum

<400> SEQUENCE: 1

```
atgggcaact tgagatcttc ttttgttttc ttcctccttg ccttggtgac ttatacttat    60
gctgcgacta tcgaggtccg aaacaactgt ccgtacaccg tttgggcggc gtcgacaccc   120
ataggcggtg ccggcgtctc gatcgaggcc aaacttgggt gatcaatgcc accacgaggt   180
actaaaatgg cacgtgtatg gggccgtact aattgtaact tcaatgctgc tggtaggggt   240
acgtgccaaa ccggtgactg tggtggagtc ctacagtgca ccgggtgggg taaaccacca   300
aacaccttgg ctgaatacgc tttggaccaa tcagtggtt tagatttctg ggacatttct    360
ttacttgatg gattcaacat tccgatcact ttccccacta accctagtgg agggaaatgc   420
catgcattat gtacggctat aaacggcgaa tgtcccgcgg aacttagggt tcctggagga   480
tgtaataacc cttgtactac attcggagga caacaatatt gttgcacaca agaccttgt    540
ggtcctacat ttttctcaaa attttttcaaa caaagatgcc ctgatgccta tagctaccca   600
caagatgatc ctactagcac ttttacttgc cctggtggta gtacaaatta tagggttatc   660
ttttgtccta atggtcaagc tcacccaaat tttcccttgg aaatgcctgg aagtgatgaa   720
gtggctaagt ag                                                      732

<210> SEQ ID NO 2
<211> LENGTH: 33
<212> TYPE: DNA
<213> ORGANISM: Artificial
<220> FEATURE:
<223> OTHER INFORMATION: Forward primer for Nicotiana tabacum osmotin
      gene

<400> SEQUENCE: 2
cacacatatg ggatccgcga ctatcgaggt ccg                                33

<210> SEQ ID NO 3
<211> LENGTH: 32
<212> TYPE: DNA
<213> ORGANISM: Artificial
<220> FEATURE:
<223> OTHER INFORMATION: Reverse primer for Nicotiana tabacum osmotin
      gene

<400> SEQUENCE: 3
tcgaattctt agccacttca tcacttccag gc                                 32

<210> SEQ ID NO 4
<211> LENGTH: 243
<212> TYPE: PRT
<213> ORGANISM: Nicotiana tabacum

<400> SEQUENCE: 4

Met Gly Asn Leu Arg Ser Ser Phe Val Phe Leu Leu Ala Leu Val
 1               5                  10                  15

Thr Tyr Thr Tyr Ala Ala Thr Ile Glu Val Arg Asn Asn Cys Pro Tyr
                 20                  25                  30

Thr Val Trp Ala Ala Ser Thr Pro Ile Gly Gly Gly Arg Leu Asp
                 35                  40                  45

Arg Gly Gln Thr Trp Val Ile Asn Ala Pro Arg Gly Thr Lys Met Ala
 50                  55                  60

Arg Val Trp Gly Arg Thr Asn Cys Asn Phe Asn Ala Ala Gly Arg Gly
 65                  70                  75                  80

Thr Cys Gln Thr Gly Asp Cys Gly Gly Val Leu Gln Cys Thr Gly Trp
                 85                  90                  95

Gly Lys Pro Pro Asn Thr Leu Ala Glu Tyr Ala Leu Asp Gln Phe Ser
                100                 105                 110
```

```
Gly Leu Asp Phe Trp Asp Ile Ser Leu Leu Asp Gly Phe Asn Ile Pro
            115                 120                 125

Ile Thr Phe Pro Thr Asn Pro Ser Gly Gly Lys Cys His Ala Leu Cys
        130                 135                 140

Thr Ala Ile Asn Gly Glu Cys Pro Ala Glu Leu Arg Val Pro Gly Gly
145                 150                 155                 160

Cys Asn Asn Pro Cys Thr Thr Phe Gly Gly Gln Gln Tyr Cys Cys Thr
                165                 170                 175

Gln Arg Pro Cys Gly Pro Thr Phe Phe Ser Lys Phe Lys Gln Arg
                180                 185                 190

Cys Pro Asp Ala Tyr Ser Tyr Pro Gln Asp Pro Thr Ser Thr Phe
                195                 200                 205

Thr Cys Pro Gly Gly Ser Thr Asn Tyr Arg Val Ile Phe Cys Pro Asn
        210                 215                 220

Gly Gln Ala His Pro Asn Phe Pro Leu Glu Met Pro Gly Ser Asp Glu
225                 230                 235                 240

Val Ala Lys

<210> SEQ ID NO 5
<211> LENGTH: 222
<212> TYPE: PRT
<213> ORGANISM: Nicotiana tabacum

<400> SEQUENCE: 5

Ala Thr Ile Glu Val Arg Asn Asn Cys Pro Tyr Thr Val Trp Ala Ala
1               5                   10                  15

Ser Thr Pro Ile Gly Gly Gly Arg Arg Leu Asp Arg Gly Gln Thr Trp
                20                  25                  30

Val Ile Asn Ala Pro Arg Gly Thr Lys Met Ala Arg Val Trp Gly Arg
            35                  40                  45

Thr Asn Cys Asn Phe Asn Ala Ala Gly Arg Gly Thr Cys Gln Thr Gly
        50                  55                  60

Asp Cys Gly Gly Val Leu Gln Cys Thr Gly Trp Gly Lys Pro Pro Asn
65                  70                  75                  80

Thr Leu Ala Glu Tyr Ala Leu Asp Gln Phe Ser Gly Leu Asp Phe Trp
                85                  90                  95

Asp Ile Ser Leu Leu Asp Gly Phe Asn Ile Pro Ile Thr Phe Pro Thr
                100                 105                 110

Asn Pro Ser Gly Gly Lys Cys His Ala Leu Cys Thr Ala Ile Asn Gly
            115                 120                 125

Glu Cys Pro Ala Glu Leu Arg Val Pro Gly Gly Cys Asn Asn Pro Cys
        130                 135                 140

Thr Thr Phe Gly Gly Gln Gln Tyr Cys Cys Thr Gln Arg Pro Cys Gly
145                 150                 155                 160

Pro Thr Phe Phe Ser Lys Phe Phe Lys Gln Arg Cys Pro Asp Ala Tyr
                165                 170                 175

Ser Tyr Pro Gln Asp Asp Pro Thr Ser Thr Phe Thr Cys Pro Gly Gly
                180                 185                 190

Ser Thr Asn Tyr Arg Val Ile Phe Cys Pro Asn Gly Gln Ala His Pro
            195                 200                 205

Asn Phe Pro Leu Glu Met Pro Gly Ser Asp Glu Val Ala Lys
        210                 215                 220

<210> SEQ ID NO 6
<211> LENGTH: 223
```

<212> TYPE: PRT
<213> ORGANISM: Nicotiana tabacum

<400> SEQUENCE: 6

```
Met Gly Asn Leu Arg Ser Ser Phe Val Phe Leu Leu Ala Leu Val
1               5                   10                  15

Thr Tyr Thr Tyr Ala Ala Thr Ile Glu Val Arg Asn Asn Cys Pro Tyr
            20                  25                  30

Thr Val Trp Ala Ala Ser Thr Pro Ile Gly Gly Arg Arg Leu Asp
            35                  40                  45

Arg Gly Gln Thr Trp Val Ile Asn Ala Pro Arg Gly Thr Lys Met Ala
            50                  55                  60

Arg Val Trp Gly Arg Thr Asn Cys Asn Phe Asn Ala Ala Gly Arg Gly
65                  70                  75                  80

Thr Cys Gln Thr Gly Asp Cys Gly Gly Val Leu Gln Cys Thr Gly Trp
            85                  90                  95

Gly Lys Pro Pro Asn Thr Leu Ala Glu Tyr Ala Leu Asp Gln Phe Ser
            100                 105                 110

Gly Leu Asp Phe Trp Asp Ile Ser Leu Leu Asp Gly Phe Asn Ile Pro
            115                 120                 125

Ile Thr Phe Pro Thr Asn Pro Ser Gly Gly Lys Cys His Ala Leu Cys
            130                 135                 140

Thr Ala Ile Asn Gly Glu Cys Pro Ala Glu Leu Arg Val Pro Gly Gly
145                 150                 155                 160

Cys Asn Asn Pro Cys Thr Thr Phe Gly Gly Gln Gln Tyr Cys Cys Thr
                165                 170                 175

Gln Arg Pro Cys Gly Pro Thr Phe Phe Ser Lys Phe Lys Gln Arg
                180                 185                 190

Cys Pro Asp Ala Tyr Ser Tyr Pro Gln Asp Pro Thr Ser Thr Phe
                195                 200                 205

Thr Cys Pro Gly Gly Ser Thr Asn Tyr Arg Val Ile Phe Cys Pro
            210                 215                 220
```

<210> SEQ ID NO 7
<211> LENGTH: 202
<212> TYPE: PRT
<213> ORGANISM: Nicotiana tabacum

<400> SEQUENCE: 7

```
Ala Thr Ile Glu Val Arg Asn Asn Cys Pro Tyr Thr Val Trp Ala Ala
1               5                   10                  15

Ser Thr Pro Ile Gly Gly Gly Arg Arg Leu Asp Arg Gly Gln Thr Trp
            20                  25                  30

Val Ile Asn Ala Pro Arg Gly Thr Lys Met Ala Arg Val Trp Gly Arg
            35                  40                  45

Thr Asn Cys Asn Phe Asn Ala Ala Gly Arg Gly Thr Cys Gln Thr Gly
            50                  55                  60

Asp Cys Gly Gly Val Leu Gln Cys Thr Gly Trp Gly Lys Pro Pro Asn
65                  70                  75                  80

Thr Leu Ala Glu Tyr Ala Leu Asp Gln Phe Ser Gly Leu Asp Phe Trp
            85                  90                  95

Asp Ile Ser Leu Leu Asp Gly Phe Asn Ile Pro Ile Thr Phe Pro Thr
            100                 105                 110

Asn Pro Ser Gly Gly Lys Cys His Ala Leu Cys Thr Ala Ile Asn Gly
            115                 120                 125

Glu Cys Pro Ala Glu Leu Arg Val Pro Gly Gly Cys Asn Asn Pro Cys
```

```
                    130                 135                 140
Thr Thr Phe Gly Gly Gln Gln Tyr Cys Cys Thr Gln Arg Pro Cys Gly
145                 150                 155                 160

Pro Thr Phe Phe Ser Lys Phe Phe Lys Gln Arg Cys Pro Asp Ala Tyr
                165                 170                 175

Ser Tyr Pro Gln Asp Asp Pro Thr Ser Thr Phe Thr Cys Pro Gly Gly
                180                 185                 190

Ser Thr Asn Tyr Arg Val Ile Phe Cys Pro
            195                 200

<210> SEQ ID NO 8
<211> LENGTH: 228
<212> TYPE: PRT
<213> ORGANISM: Solanum nigrum

<400> SEQUENCE: 8

Met Gly Tyr Ser Arg Ser Ser Phe Val Phe Leu Leu Thr Phe Val
1               5                   10                  15

Thr Tyr Thr Tyr Ala Thr Ser Phe Glu Val Arg Asn Asn Cys Pro Tyr
                20                  25                  30

Thr Val Trp Ala Ala Ser Thr Pro Ile Gly Gly Gly Arg Leu Asp
            35                  40                  45

Arg Gly Gln Thr Trp Val Ile Asn Ala Pro Arg Gly Thr Ser Met Ala
50                  55                  60

Arg Ile Trp Gly Arg Thr Asn Cys Asn Phe Asp Gly Ala Gly Arg Gly
65                  70                  75                  80

Ser Cys Gln Thr Gly Asp Cys Gly Gly Val Leu Gln Cys Thr Gly Trp
                85                  90                  95

Gly Lys Pro Pro Asn Thr Leu Ala Glu Tyr Ala Leu Asn Gln Phe Ser
            100                 105                 110

Asn Leu Asp Phe Trp Asp Ile Ser Leu Val Asp Gly Phe Asn Ile Pro
            115                 120                 125

Met Thr Phe Ala Pro Thr Asn Pro Ser Gly Gly Lys Cys His Ser Ile
130                 135                 140

Gln Cys Thr Ala Asn Ile Asn Gly Glu Cys Pro Ala Ala Leu Arg Val
145                 150                 155                 160

Pro Gly Gly Cys Asn Asn Pro Cys Thr Thr Phe Gly Gly Gln Gln Tyr
                165                 170                 175

Cys Cys Thr Gln Gly Pro Cys Gly Pro Thr Glu Leu Ser Lys Phe Phe
            180                 185                 190

Lys Gln Arg Cys Pro Asp Ala Tyr Ser Tyr Pro Gln Asp Asp Pro Thr
            195                 200                 205

Ser Thr Phe Thr Cys Pro Ser Asp Ser Thr Asn Tyr Arg Val Val Phe
            210                 215                 220

Cys Pro Asn Gly
225

<210> SEQ ID NO 9
<211> LENGTH: 204
<212> TYPE: PRT
<213> ORGANISM: Artificial
<220> FEATURE:
<223> OTHER INFORMATION: Consensus amino acid sequence for comparison of
      Solanum nigrum osmotin-like protein and Nicotiana tabacum osmotin
      protein
<220> FEATURE:
<221> NAME/KEY: VARIANT
<222> LOCATION: (2)..(2)
<223> OTHER INFORMATION: "X" is "F" or "I"
```

```
<220> FEATURE:
<221> NAME/KEY: VARIANT
<222> LOCATION: (40)..(40)
<223> OTHER INFORMATION: "X" is "S" or "K"
<220> FEATURE:
<221> NAME/KEY: VARIANT
<222> LOCATION: (53)..(53)
<223> OTHER INFORMATION: "X" is "D" or "N"
<220> FEATURE:
<221> NAME/KEY: VARIANT
<222> LOCATION: (87)..(87)
<223> OTHER INFORMATION: "X" is "N" or "D"
<220> FEATURE:
<221> NAME/KEY: VARIANT
<222> LOCATION: (91)..(91)
<223> OTHER INFORMATION: "X" is "N" or "G"
<220> FEATURE:
<221> NAME/KEY: VARIANT
<222> LOCATION: (123)..(123)
<223> OTHER INFORMATION: "X" is "Q" or "H"
<220> FEATURE:
<221> NAME/KEY: VARIANT
<222> LOCATION: (134)..(134)
<223> OTHER INFORMATION: "X" is "A" or "R"
<220> FEATURE:
<221> NAME/KEY: VARIANT
<222> LOCATION: (135)..(135)
<223> OTHER INFORMATION: "X" is "A" or "E"
<220> FEATURE:
<221> NAME/KEY: VARIANT
<222> LOCATION: (165)..(165)
<223> OTHER INFORMATION: "X" is "E" or "F"
<220> FEATURE:
<221> NAME/KEY: VARIANT
<222> LOCATION: (166)..(166)
<223> OTHER INFORMATION: "X" is "L" or "F"
<220> FEATURE:
<221> NAME/KEY: VARIANT
<222> LOCATION: (193)..(193)
<223> OTHER INFORMATION: "X" is "S" or "G"
<220> FEATURE:
<221> NAME/KEY: VARIANT
<222> LOCATION: (194)..(194)
<223> OTHER INFORMATION: "X" is "D" or "G"

<400> SEQUENCE: 9

Ser Xaa Glu Val Arg Asn Asn Cys Pro Thr Tyr Val Trp Ala Ala Ser
1               5                   10                  15

Thr Pro Ile Gly Gly Gly Arg Arg Leu Asp Arg Gly Gln Thr Trp Val
            20                  25                  30

Ile Asn Ala Pro Arg Gly Thr Xaa Met Ala Arg Ile Trp Gly Arg Thr
        35                  40                  45

Asn Cys Asn Phe Xaa Ala Ala Gly Arg Gly Ser Cys Gln Thr Gly Asp
50                  55                  60

Cys Gly Gly Val Leu Gln Cys Thr Gly Trp Gly Lys Pro Pro Asn Thr
65                  70                  75                  80

Leu Ala Glu Tyr Ala Leu Xaa Gln Phe Ser Xaa Leu Asp Phe Trp Asp
                85                  90                  95

Ile Ser Leu Val Asp Gly Phe Asn Ile Pro Met Thr Phe Ala Pro Thr
                100                 105                 110

Asn Pro Ser Gly Gly Lys Cys His Ala Ile Xaa Cys Thr Ala Asn Ile
            115                 120                 125

Asn Gly Glu Cys Pro Xaa Xaa Leu Arg Val Pro Gly Gly Cys Asn Asn
    130                 135                 140

Pro Cys Thr Thr Phe Gly Gly Gln Gln Tyr Cys Cys Thr Gln Gly Pro
145                 150                 155                 160

Cys Gly Pro Thr Xaa Xaa Ser Lys Phe Phe Lys Gln Arg Cys Pro Asp
                165                 170                 175
```

```
-continued

Ala Tyr Ser Tyr Pro Gln Asp Pro Thr Ser Thr Phe Thr Cys Pro
            180                 185                 190

Xaa Xaa Ser Thr Asn Tyr Arg Val Ile Phe Cys Pro
        195                 200
```

MICROBIAL EXPRESSION OF TOBACCO OSMOTIN FOR BIOCIDAL AND MEDICAL APPLICATIONS

CROSS-REFERENCE TO RELATED APPLICATIONS

The present application claims the benefit under 35 U.S.C. §119(e) to U.S. Provisional Application No. 61/287,583 filed on Dec. 17, 2009, the contents of which are incorporated herein by reference.

STATEMENT REGARDING FEDERALLY SPONSORED RESEARCH OR DEVELOPMENT

This invention was made with government support under Grant No. 2008-34605-19275 awarded by the United States Department of Agriculture. The government has certain rights in the invention.

BACKGROUND

The field of the present invention relates to methods of expressing relatively high levels of recombinant tobacco osmotin in a microorganism. The recombinant tobacco osmotin thereby expressed may be purified and utilized as a biocidal agent or a therapeutic agent in medical applications.

Pathogenesis-related proteins (PR) are produced by plants in response to environmental stress, such as extremes of salinity, and pathogen infections (Kononowicz et al. 1992). Because of the nature and purpose of host plants, there is a great potential for some PR proteins to be used in controlling food borne pathogens. Among PR proteins, osmotin is one of the best studied which has shown biocidal activity (Narasimhan et al. 2005; Narasimhan et al. 2001). Because the biocidal mechanisms of osmotin are somewhat hormonal, theoretically, osmotin should be more potent than enzymatic and enzyme-inhibitory biocides. Moreover, osmotin is safe for human intake because of its existence in many plants, meaning that humans frequently consume osmotin in diets of vegetables, fruit, or nuts.

Recent studies of the fungicidal mechanisms of tobacco osmotin (OSM) have shown that OSM binds to yeast surface protein, PHO36, and mediates the signal cascades leading to apoptosis. Because PHO36 is homologous to human adiponectin receptor, OSM has been proposed to be an analogue of adiponectin carrying similar functions in human (Narasimhan et al., 2005). Despite the early discovery and characterization of OSM (Singh et al., 1987) and its potential applications in treating fungal infections, diabetes, and obesity in humans (Min et al., 2004; Narasimhan et al., 2005) and in controlling food borne pathogens, osmotin has never been widely investigated or applied because of its limited availability. Osmotin has proved to be refractory to common systems for overexpression. Currently, the only source or OSM is a purified form from salt-adapted tobacco cell culture of Wisconsin 38 (Singh et al., 1987).

A transgenic plant that includes OSM driven by a strong promoter, such as cauliflower mosaic virus, theoretically should be a good source for OSM. Liu et al. (1994) successfully obtained OSM overexpressed potato by *Agrobacterium*-mediated transformation. However, no one has reported the production of OSM from a transgenic plant. OSM has been suggested to form multimers (up to 20 mers, Singh, personal communication). This makes OSM extraction from plant tissues and elution in chromatographic purification difficult if not impossible. Therefore, scientists have been seeking more facile expression systems, such as *E. coli*. However, OSM is somewhat toxic to bacteria, resulting in a very low yield in bacterial expression systems. For these reasons, better expression systems for OSM are desirable.

SUMMARY

Disclosed herein are recombinant tobacco osmotin polypeptides and methods for expressing tobacco osmotin polypeptides in microbial host cells. The recombinant tobacco osmotin polypeptides produced by the methods disclosed herein may be utilized as biocides or as therapeutic agents in medicaments.

In some embodiments, the methods for expressing the recombinant tobacco osmotin polypeptides include the following steps: (a) growing in culture media microbial host cells transformed with a vector that inducibly expresses the tobacco osmotin polypeptide; (b) inducing expression of the tobacco osmotin polypeptide; (c) optionally adjusting pH of the culture media after inducing expression of the tobacco osmotin polypeptide, for example adjusting the pH upward to about 6.5-7.5 for some microbes such as bacteria (preferably about 6.8-7.2, more preferably about 6.8-7.0), or adjusting the pH upward to about 5.5-6.5 for other microbes such as yeast (preferably about 5.7-6.3, more preferably about 5.9-6.1); and (d) isolating the tobacco osmotin polypeptide, where at least about 50 mg tobacco osmotin polypeptide per liter of culture media is isolated (preferably at least about 200 mg per liter of culture media is isolated, more preferably at least about 300 mg per liter of culture media is isolated).

In some embodiments of the disclosed methods, the pH of the culture media is adjusted upward after inducing expression of the tobacco osmotin polypeptide. The pH of the culture media may be adjusted continuously or at discrete time points. For example, in some embodiments, the pH of the culture media may be adjusted upward a first time to about 6.5-7.5 at about 1-3 hours after inducing expression of the tobacco osmotin polypeptide, and then the pH of the culture media may be adjusted upward a second time to about 6.5-7.5 at about 3-5 hours after inducing expression of the tobacco osmotin polypeptide. In further embodiments, the pH of the culture may be adjusted upward a third time to about 6.5-7.5 at about 5-7 hours after inducing expression of the tobacco osmotin polypeptide. The pH of the media may be adjusted upwards via addition of a base such as NaOH. If necessary, the pH of the media may be adjusted downwards via addition of an acid such as HCl. However, typically the pH of the media is adjusted upward.

The methods include inducing expression of the tobacco osmotin polypeptide in the host cells. In some embodiments, expression of the tobacco osmotin polypeptide may be induced by adding an inducing agents such as isopropyl β-D-1-thiogalactopyranoside to the culture media, optionally when the culture media has an $OD_{650}$ of between about 1-2. In other embodiments, expression of the tobacco osmotin polypeptide may be induced by, adding an inducing agent such as alcohol (e.g., methanol) to the culture media. Expression of the tobacco osmotin polypeptide may be induced directly by the inducing agent. For example, the inducing agent may directly induce expression from the vector by inducing expression from a promoter present in the vector. Alternatively, expression of the tobacco osmotin may be induced indirectly by the inducing agent. For example, the inducing agent may directly induce expression of an enzyme (e.g., T7 RNA polymerase) that is required for expression of the tobacco osmotin polypeptide from the vector, thereby indirectly inducing expression of the tobacco osmotin polypeptide.

The transformed host cells are grown in suitable media as known in the art such as lysogeny broth (LB) media. The media may be supplemented with agents that promote expression, growth, or viability of the host cells. In some embodiments, the culture media comprises at least about 2 µM $Fe^{3+}$ (preferably at least about 5 or 10 µM $Fe^{3+}$). For example, the culture media may comprise at least about 2 µM $FeCl_3$ (preferably at least about 5 or 10 µM $FeCl_3$). The media may comprise a range of $Fe^{3+}$. In some embodiments, the culture media comprises about 2-20 µM $Fe^{3+}$. For example, the culture media may comprise about 2-20 µM $Fe^{3+}FeCl_3$.

The present methods are utilized to produce a recombinant tobacco osmotin polypeptide. In some embodiments of the methods, the host cells are transformed with a vector that encodes and expresses a tobacco osmotin polypeptide comprising any of SEQ ID NOs:4-9 or a variant thereof having at least 95% amino acid sequence identity to any of SEQ ID NO:4-9 and exhibiting one or more functional activities associated with osmotin such as biocidal activity. In further embodiments, the tobacco osmotin polypeptide produced by the methods disclosed herein has anti-fungal activity and inhibits growth of a culture of one or more yeast species selected from a group consisting of *Candida albicans, Cryptococcus neoformans, Saccharomyces cerevisiase,* and *Pichia methanolica*. Preferably, the tobacco osmotin polypeptide inhibits 50% of growth of the culture when the tobacco osmotin polypeptide is present in the culture at a concentration of no more than about 300 µg/ml (preferably no more than about 200 µg/ml, even more preferably no more than about 100 µg/ml). In even further embodiments, the tobacco osmotin polypeptide inhibits 10% of growth of the culture when the tobacco osmotin polypeptide is present in the culture at a concentration of no more than about 100 µg/ml (preferably no more than about 50 µg/ml, even more preferably no more than about 1 µg/ml).

Suitable host cells for the methods disclosed herein may include bacteria. Suitable bacteria may include, but are not limited to, *E. coli*. In some embodiments, the *E. coil* host cell inducibly expresses T7 RNA polymerase in the presence of IPTG and the vector expresses the tobacco osmotin polypeptide in the presence of T7 RNA polymerase. In further embodiments, the tobacco osmotin polypeptide is expressed in inclusion bodies of the *E. coli* and the tobacco osmotin polypeptide is isolated via isolating the inclusion bodies and solubilizing the tobacco osmotin polypeptide in the inclusion bodies.

Suitable host cells for the methods disclosed herein also may include yeast. Suitable yeast may include, but are not limited to, *Pichia methanolica*.

DETAILED DESCRIPTION

Disclosed herein are recombinant tobacco osmotin and methods for expressing recombinant tobacco osmotin in microbial expression systems. The disclosed methods may be described using several definitions as discussed below.

Unless otherwise specified or indicated by context, the terms "a", "an", and "the" mean "one or more." In addition, singular nouns such as "polypeptide" should be interpreted to mean "one or more polypeptides," unless otherwise specified or indicated by context.

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≦10% of the particular term and "substantially" and "significantly" will mean plus or minus >10% of the particular term.

As used herein, the terms "include" and "including" have the same meaning as the terms "comprise" and "comprising."

The present methods relate to recombinant forms of tobacco osmotin. The full-length coding sequence of tobacco osmotin cDNA (i.e., *Nicotiana tabacum* osmotin) is provided at GenBank Accession No: M29279.1 and has been reported by Singh et al., Plant Physiol. 90 (3), 1096-1101 (1989), and Melchers et al., Plant Molecular Biology 21: 583-593, 1993, the contents of which are incorporated by reference in their entireties. (See also, SEQ ID NOS: 1 and 4).

The methods disclosed herein are utilized to produce a recombinant "tobacco osmotin polypeptide. As used herein, the term "tobacco osmotin polypeptide" includes: full-length tobacco osmotin protein; processed forms of tobacco osmotin protein lacking the N-terminal signal sequence (e.g., lacking a sequence of from amino acid 1 to about amino acid 21 such as SEQ ID NO:5); processed forms of tobacco osmotin protein lacking the C-terminal vacuolar targeting sequence (e.g., lacking a sequence from about amino acid 223 to amino acid 243 such as SEQ ID NO:6); and processed forms of tobacco osmotin protein lacking both the N-terminal signal sequence and the C-terminal vacuolar targeting sequence (e.g., lacking a sequence from amino acid 1 to about amino acid 21 and lacking a sequence from about amino acid 223 to amino acid 243 such as SEQ ID NO:7); and "variants," "mutants," and "derivatives" thereof as discussed herein. The tobacco osmotin polypeptide produced by the methods disclosed herein preferably exhibits one or more functional activities associated with tobacco osmotin. For example, functional activities associated with tobacco osmotin may include biocidal activity, which may include anti-fungal activity and may be measured as disclosed herein. Functional activities associated with tobacco osmotin also may include binding to $Fe^{3+}$, which may be measured as disclosed herein.

The presently disclosed methods related to an osmotin protein, polypeptide, or peptide that is recombinant, expressed in a host cell, and isolated or purified. As utilized herein, a protein, polypeptide, and peptide refer to a molecule comprising a chain of amino acid residues joined by amide linkages. The term "amino acid residue," includes but is not limited to amino acid residues contained in the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues. The terms "protein," "polypeptide," and "peptide" may be referred to interchangeably herein. However, the terms may be distinguished as follows. A "protein" typically refers to the end product of transcription, translation, and post-translation modifications in a cell. Accordingly, a protein typically exhibits a biological function. A polypeptide is typically an amino acid chain of length >100 amino acids (Garrett & Grisham, Biochemistry, $2^{nd}$ edition, 1999, Brooks/Cole, 110, which is incorporated herein by reference in its entirety). A polypeptide, as contemplated herein, may comprise, but is not limited to, 100, 101, 102, 103, 104, 105, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or more amino acid residues. A peptide, in contrast to a polypeptide, typically is a short polymer of amino acids, of a length typically of 20 or less amino acids (Garrett & Grisham, Biochemistry, $2^{nd}$ edition, 1999, Brooks/Cole, 110, which is incorporated herein by reference in its entirety). In some embodiments, a peptide as contemplated herein may include no more than about 10, 11, 12, 13, 14, 15, 16, 17, 18, 19, or 20 amino acids.

The recombinant osmotin proteins, polypeptides, or peptides disclosed herein are encoded by polynucleotide sequences comprising nucleic acid. The terms "nucleic acid" and "nucleic acid sequence" refer to a nucleotide, oligonucleotide, polynucleotide (which terms may be used interchangeably), or any fragment thereof. These phrases also refer to DNA or RNA of genomic or synthetic origin (which may be single-stranded or double-stranded and may represent the sense or the antisense strand).

As utilized herein, A "full length" polynucleotide sequence is one containing at least a translation initiation codon (e.g., methionine) followed by an open reading frame and a translation termination codon. A "full length" polynucleotide sequence encodes a "full length" polypeptide sequence.

The words "insertion" and "addition" refer to changes in an amino acid or nucleotide sequence resulting in the addition of one or more amino acid residues or nucleotides, respectively. An insertion or addition may refer to 1, 2, 3, 4, 5, 10, 20, 30, 40, 50, 60, 70, 80, 90, 100, 150, or 200 amino acid residues or nucleotides.

A "deletion" refers to a change in the amino acid or nucleotide sequence that results in the absence of one or more amino acid residues or nucleotides. A deletion removes at least 1, 2, 3, 4, 5, 10, 20, 50, 100, or 200 amino acids residues or nucleotides. A deletion may include an internal deletion or a terminal deletion (e.g., an N-terminal truncation or a C-terminal truncation such of a reference polypeptide or a 5'-terminal or 3'-terminal truncation of a reference polynucleotide).

A "fragment" is a portion of an amino acid sequence or a polynucleotide which is identical in sequence to but shorter in length than a reference sequence. A fragment may comprise up to the entire length of the reference sequence, minus at least one nucleotide/amino acid residue. For example, a fragment may comprise from 5 to 1000 contiguous nucleotides or contiguous amino acid residues of a reference polynucleotide or reference polypeptide, respectively. In some embodiments, a fragment may comprise at least 5, 10, 15, 20, 25, 30, 40, 50, 60, 70, 80, 90, 100, 150, 250, or 500 contiguous nucleotides or contiguous amino acid residues of a reference polynucleotide or reference polypeptide, respectively. Fragments may be preferentially selected from certain regions of a molecule. The term "at least a fragment" encompasses the full length polynucleotide or full length polypeptide.

A "fragment" or a "truncated form" of a protein or a polypeptide as contemplated herein refers to a contiguous portion of the amino acid sequence of the protein or polypeptide. Further, A "fragment" or a "truncated form" of a protein or polypeptide refers to less than a full-length amino acid sequence of the protein or polypeptide (e.g., where the full-length amino acid sequence is truncated at the N-terminus, the C-terminus, or both termini). For example, a "fragment" or a "truncated form" of a protein or polypeptide may comprise or consist of a 5-200, 5-150, 5-100, 5-50, 5-25, 5-15, 10-200, 10-150, 10-100, 10-50, 10-25, or 10-15 contiguous amino acid sequence of the full-length protein or polypeptide.

As used herein, "homology" refers to sequence similarity or, interchangeably, sequence identity, between two or more polynucleotide sequences or two or more polypeptide sequences. Homology, sequence similarity, and percentage sequence identity may be determined using methods in the art and described herein.

The terms "percent identity" and "% identity," as applied to polynucleotide sequences, refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Percent identity for a nucleic acid sequence may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403 410), which is available from several sources, including the NCBI, Bethesda, Md., at its website. The BLAST software suite includes various sequence analysis programs including "blastn," that is used to align a known polynucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively at the NCBI website. The "BLAST 2 Sequences" tool can be used for both blastn and blastp (discussed below).

Percent identity may be measured over the length of an entire defined polynucleotide sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

A "variant," "mutant," or "derivative" of a particular nucleic acid sequence may be defined as a nucleic acid sequence having at least 50% sequence identity to the particular nucleic acid sequence (e.g., any of SEQ ID NOs:1-3) over a certain length of one of the nucleic acid sequences using blastn with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of nucleic acids may show, for example, at least 60%, at least 70%, at least 80%, at least 85%, at least 90%, at least 91%, at least 92%, at least 93%, at least 94%, at least 95%, at least 96%, at least 97%, at least 98%, or at least 99% or greater sequence identity over a certain defined length.

Nucleic acid sequences that do not show a high degree of identity may nevertheless encode similar amino acid sequences due to the degeneracy of the genetic code. It is understood that changes in a nucleic acid sequence can be made using this degeneracy to produce multiple nucleic acid sequences that all encode substantially the same protein.

The phrases "percent identity" and "% identity," as applied to polypeptide sequences, refer to the percentage of residue matches between at least two polypeptide sequences aligned using a standardized algorithm. Methods of polypeptide sequence alignment are well-known. Some alignment methods take into account conservative amino acid substitutions. Such conservative substitutions, explained in more detail above, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403 410), which is available from several sources, including the NCBI, Bethesda, Md., at its website. The BLAST software suite includes various sequence analysis programs including "blastp," that is used to align a known amino acid sequence with other amino acids sequences from a variety of databases.

Percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

A "variant," "mutant," or "derivative" of a particular polypeptide sequence is defined as a polypeptide sequence having at least 50% sequence identity to the particular polypeptide sequence (e.g., any of SEQ ID NOs:4-9) over a certain length of one of the polypeptide sequences using blastp with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of polypeptides may show, for example, at least 60%, at least 70%, at least 80%, at least 90%, at least 91%, at least 92%, at least 93%, at least 94%, at least 95%, at least 96%, at least 97%, at least 98%, or at least 99% or greater sequence identity over a certain defined length of one of the polypeptides. A "variant" or a "derivative" may have substantially the same functional activity as a reference polypeptide. For example, a variant or derivative of tobacco osmotin may exhibit one or more functional activities of tobacco osmotin (e.g., biocidal activity and $Fe^{3+}$-binding activity as disclosed herein).

The amino acid sequences contemplated herein may include conservative amino acid substitutions relative to a reference amino acid sequence. For example, a variant, mutant, or derivative polypeptide may include conservative amino acid substitutions relative to a reference polypeptide. "Conservative amino acid substitutions" are those substitutions that are predicted to interfere least with the properties of the reference polypeptide. In other words, conservative amino acid substitutions substantially conserve the structure and the function of the reference protein. A list of exemplary conservative amino acid substitutions is provided below:

| Original Residue | Conservative Substitution |
|---|---|
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

The recombinant tobacco osmotin polypeptides disclosed herein optionally may include a peptide tag (e.g., a peptide tag fused at its C-terminus). Suitable peptide tags may include, but are not limited to a 6×His tag, a hemaglutinin tag, a FLAG tag, a glutathione-S-transferase tag, a green fluorescent protein tag, a maltose binding protein tag, a chitin binding protein tag, or another functional sequence of amino acids.

As utilized herein, a "recombinant nucleic acid" is a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques such as those described in Sambrook, J. et al. (1989) Molecular Cloning: A Laboratory Manual, $2^{nd}$ ed., vol. 13, Cold Spring Harbor Press, Plainview N.Y. The term recombinant includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector that is used, for example, to transform a cell.

As used herein, "operably linked" refers to the situation in which a first nucleic acid sequence is placed in a functional relationship with a second nucleic acid sequence. For instance, a promoter is operably linked to a coding sequence if the promoter affects the transcription or expression of the coding sequence. Operably linked DNA sequences may be in close proximity or contiguous and, where necessary to join two protein coding regions, in the same reading frame.

"Substantially isolated or purified" nucleic acid or amino acid sequences are contemplated herein. The term "substantially isolated or purified" refers to nucleic acid or amino acid sequences that are removed from their natural environment, and are at least 60% free, preferably at least 75% free, and more preferably at least 90% free, even more preferably at least 95% free from other components with which they are naturally associated.

"Transformation" describes a process by which exogenous DNA is introduced into a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, bacteriophage or viral infection, electroporation, heat shock, lipofection, and particle bombardment. The term "transformed cells" includes stably transformed cells in which the inserted DNA is capable of replication either as an autonomously replicating plasmid or as part of the host chromosome, as well as transiently transformed cells which express the inserted DNA or RNA for limited periods of time.

Microbial expression vectors that express a tobacco osmotin polypeptide also are contemplated herein. Vectors may be used to transform appropriate host cells (e.g., *E. coli*). The transformed host cell may be cultivated or fermented such that the tobacco osmotin polypeptide is expressed constitutively or after adding a reagent that induces expression (e.g., via an inducible promoter). The tobacco osmotin polypeptide may be further processed after expression. Expression vectors as contemplated herein may include control sequences that modulate expression of the tobacco osmotin polypeptide. Expression control sequences may include constitutive or inducible promoters (e.g., T3, T7, Lac, trp, or phoA), ribosome binding sites, or transcription terminators. The vectors disclosed herein may be utilized to transform host cells. Suitable host cells include microbial host cells (e.g., bacterial or fungal host cells). Suitable bacteria include, but are not limited to: Gram-negative bacteria such as *Escherichia* species (e.g. *E. coli*), other Gram-negative bacteria, (e.g., *Pseudomonas* sp., such as *Pseudomonas aeruginosa*, or *Caulobacter* sp., such as *Caulobacter crescentus*), or Gram-positive bacteria (e.g., *Bacillus* sp., in particular *Bacillus subtilis*). Suitable fungal host cells include yeast cells (e.g., *Pichia methanolica*). Expression of a recombinant laccase protein in *Pichia methanolica* is described, for example, in Guo et al., Appl. Microbiol. Biotechnol. (2005) 69:178-183, the content of which is incorporated herein by reference in its entirety.

Also disclosed are methods for expressing, preparing, isolating, separating, or purifying tobacco osmotin polypeptides. The steps of the methods may include: (i) cultivating, growing, or fermenting a transformed host cell (e.g., a bacterial host cell or fungal host cell as contemplated herein) which comprises an expression vector (as contemplated herein) which in turn comprises a nucleic acid molecule encoding a tobacco osmotin polypeptide (as contemplated herein), wherein cultivation occurs under conditions which cause expression of the tobacco osmotin polypeptide; and (ii) isolating, separating, or purifying the tobacco osmotin polypeptide. The transformed bacterial or fungal host cell may be cultivated or fermented using methods known in the art in order to express the tobacco osmotin polypeptide. The tobacco osmotin polypeptide may be isolated, separated, or purified by methods known in the art (see, e.g., M. P. Deutscher, in: Methods in Enzymology: Guide to Protein Purification, Academic Press Inc., (1990), 309-392). An exemplary isolation, separation, or purification method may include one or more of the following steps: a cell disruption step, a clarification step (e.g., via centrifugation or filtration), a chromatographic separation step, a dialysis step, and a precipitation step. For example, the tobacco osmotin polypeptides may be purified on an affinity column based on the polypeptides' affinity for metals such as cobalt.

ILLUSTRATIVE EMBODIMENTS

The following embodiments are illustrative and not intended to limit the claimed subject matter.

Embodiment 1

A method for producing a recombinant tobacco osmotin polypeptide, the method comprising: (a) growing in culture media microbial host cells transformed with a vector that inducibly expresses the tobacco osmotin polypeptide; (b) inducing expression of the tobacco osmotin polypeptide; (c) optionally adjusting pH of the culture media after inducing expression of the tobacco osmotin polypeptide, for example adjusting the pH upward to about 6.5-7.5 for some microbes such as bacteria (preferably about 6.8-7.2, more preferably about 6.8-7.0), or adjusting the pH upward to about 5.5-6.5 for other microbes such as yeast (preferably about 5.7-6.3, more preferably about 5.9-6.1); and (d) isolating the tobacco osmotin polypeptide, wherein at least about 50 mg tobacco osmotin polypeptide per liter of culture media is isolated (preferably at least about 200 mg per liter of culture media is isolated, more preferably at least about 300 mg per liter of culture media is isolated).

Embodiment 2

The method of embodiment 1, wherein the pH of the culture media is adjusted a first time to about 6.5-7.5 at about 1-3 hours after inducing expression of the tobacco osmotin polypeptide, and then the pH of the culture media is adjusted a second time to about 6.5-7.5 at about 3-5 hours after inducing expression of the tobacco osmotin polypeptide.

Embodiment 3

The method of embodiment 2, further comprising adjusting the pH of the culture a third time to about 6.5-7.5 at about 5-7 hours after inducing expression of the tobacco osmotin polypeptide.

Embodiment 4

The method of any of embodiments 1-3, comprising adjusting pH of the culture media to about 6.8-7.2 after inducing expression of the tobacco osmotin polypeptide.

Embodiment 5

The method of any of embodiments 1-4, wherein expression of the tobacco osmotin polypeptide is induced by adding isopropyl β-D-1-thiogalactopyranoside to the culture media when the culture media has an $OD_{650}$ of between about 1-2.

Embodiment 6

The method of any of embodiments 1-5, wherein expression of the tobacco osmotin polypeptide is induced either indirectly by adding isopropyl β-D-1-thiogalactopyranoside to the culture media.

Embodiment 7

The method of any of embodiments 1-6, wherein the culture media comprises at least about 2 μM $Fe^{3+}$ (preferably at least about 5 or 10 μM $Fe^{3+}$).

Embodiment 8

The method of embodiment 7, wherein the culture media comprises at least about 2 μM $FeCl_3$ (preferably at least about 5 or 10 μM $FeCl_3$).

Embodiment 9

The method of any of embodiments 1-8, wherein the culture media comprises about 2-20 μM $Fe^{3+}$.

Embodiment 10

The method of embodiment 9, wherein the culture media comprises about 2-20 μM $Fe^{3+}FeCl_3$.

Embodiment 11

The method of any of embodiments 1-10, wherein the vector encodes and/or expresses a tobacco osmotin polypeptide comprising any of SEQ ID NOs:4-9 or a variant thereof having at least 95% amino acid sequence identity to any of SEQ ID NOs:4-9 and one or more functional activities of tobacco osmotin.

Embodiment 12

The method of any of embodiments 1-11, wherein the tobacco osmotin polypeptide produced by the method has anti-fungal activity and inhibits growth of a culture of one or more yeast species selected from a group consisting of *Candida albicans*, *Cryptococcus neoformans*, *Saccharomyces cerevisiase*, and *Pichia methanolica*.

Embodiment 13

The method of embodiment 12, wherein the tobacco osmotin polypeptide inhibits 50% of growth of the culture when the tobacco osmotin polypeptide is present in the culture at a concentration of no more than about 300 μg/ml (preferably no more than about 200 μg/ml, even more preferably no more than about 100 μg/ml).

Embodiment 14

The method of embodiment 12, wherein the tobacco osmotin polypeptide inhibits 10% of growth of the culture when the tobacco osmotin polypeptide is present in the culture at a concentration of no more than about 100 μg/ml (preferably no more than about 50 μg/ml, even more preferably no more than about 1 μg/ml).

Embodiment 15

The method of any of embodiments 1-14, wherein the host cells are bacteria.

Embodiment 16

The method of embodiment 15, wherein the bacteria are *E. coli*.

Embodiment 17

The method of embodiment 16, wherein the *E. coli* inducibly expresses T7 RNA polymerase in the presence of IPTG and the vector expresses the tobacco osmotin polypeptide in the presence of T7 RNA polymerase.

Embodiment 18

The method of embodiment 16, wherein the tobacco osmotin polypeptide is expressed in inclusion bodies of the *E. coli* and the tobacco osmotin polypeptide is isolated via isolating the inclusion bodies and solubilizing the tobacco osmotin polypeptide in the inclusion bodies.

Embodiment 19

The method of any of embodiments 1-18, wherein the host cells are yeast.

Embodiment 20

The method of embodiment 19, wherein the yeast are *Pichia methanolica*.

Embodiment 21

A method for producing a recombinant tobacco osmotin polypeptide, the method comprising: (a) growing in culture media yeast transformed with a vector that inducibly expresses the tobacco osmotin polypeptide; (b) inducing expression of the tobacco osmotin polypeptide; (c) optionally adjusting pH of the culture media after inducing expression of the tobacco osmotin polypeptide; and (d) isolating tobacco osmotin polypeptide, wherein at least about 50 mg tobacco osmotin polypeptide per liter of culture media is isolated.

Embodiment 22

The method of embodiment 21, wherein the yeast is *Pichia methanolica*.

EXAMPLES

The following example is illustrative and not intended to limit the claimed subject matter. Reference is made to Tzou et al., Biotechnol. Lett. DOI 10.1007/s10529-010-0453-z, published online Nov. 3, 2010, the content of which is incorporated herein by reference in its entirety.

Expression of Truncated Tobacco Osmotin in *Escherichia coli*: Purification and Antifungal Activity Abstract Tobacco osmotin is a functional homolog of mammalian adiponectin, and has antifungal activity. This work was undertaken to produce recombinant osmotin that has previously been unsuccessful because of its toxicity. Expression of recombinant tobacco osmotin (rOSM) in *Escherichia coil* inclusion bodies was achieved by modifying growth conditions. The optimal pH for rOSM expression in ZYM 505 medium is 7.0 at $OD_{650}$ of 1.5 of culture growth. The rOSM from the inclusion body was extracted with 8 M urea, and purified using CM-cellulose and cobalt-agarose bead affinity chromatography to a high purity. Approximately 80% of the rOSM remained bound to CM-cellulose and Cobalt-agarose beads after initial elution. The yield of purified rOSM was between 40-50 mg from 2 L of culture. Repeated elution of protein from CM-cellulose and Co-agarose resulted in an increased yield of rOSM to 200 mg from 2 L culture. The purified rOSM showed variable antifungal activities against two pathogenic yeast strains; *Cryptococcus neoformans* and *Candida albicans*, and non-pathogenic strains; *Saccharomyces cerevisiae* and *Pichia methanolica*.

Introduction

Osmotin and its homolog are cationic proteins produced by plants in response to both biotic and abiotic stress. Osmotin was first identified as the most abundant protein in cultured tobacco cells adapted to low water potential by Singh et al. (1985). Regulation of both osmotin gene and protein has been extensively studied in plants. Osmotin accumulates as inclusions in the vacuolar compartment of the cultured cells adapted to low water potential of the medium, and showed homology to a sweet potato protein, thaumatin (Singh er al. 1987). Osmotin can be induced by pathogens (Stintzi et al. 1991; Woloshuk et al. 1991) and its constitutive expression in transgenic plants inhibited the growth of a number of fungal pathogens (Woloshuk et al. 1991; Vigers et al. 1992; Abad et al. 1996; Liu et al. 1994). Liu et al. (1996) showed that a C-terminal truncated osmotin was secreted outside the plasma membrane and retained antifungal activity in transgenic plants. Investigation of the mechanism of action of osmotin on fungal pathogens demonstrated a signaling role for this protein in inducing fungal cell apoptosis (Yun et al. 1997, 1998; Narsimhan et al. 2001, 2005).

Because osmotin homologs are present in all edible plants, and this protein is non-toxic to humans (Singh et al. 1987), it can be safely incorporated in food for human consumption. Despite early discovery of osmotin, its potential applications have been limited because of poor availability of the purified protein. Expression of recombinant osmotin has been hampered because of its toxicity and physical properties. *Solanum nigrum* osmotin-like protein (SnOLP) was expressed in *Escherichia coli* (Campos Mde et al. 2008) which have some differences in critical surface amino acids necessary for tobacco osmotin structure (Min et al. 2004). Since tobacco osmotin has been a model for a number of studies, and its variants do not have similar bioactivity, a protocol for expression and purification of tobacco recombinant osmotin in inclusion bodies of *E. coli* and determination of its antifungal activity is presented.

Materials and Methods

Cloning and construction of expression vector. Tobacco OSM gene (Singh et al. 1989) was used to produce a truncated amplicon. Primers OSM5_Nde (CACACATATGGGATCCGCGACTATCGAGGTCCG) and OSM3_Eco (TCGAATTCTTAGCCACTTCATCACTTCCAGGC) were designed with NdeI and EcoRI sites to produce truncated OSM.

The PCR reaction was performed with Phusion DNA polymerase (Finnzymes, Finland) using the following program; 35 cycles of 98° C. for 10 s, 58° C. for 30 s, 72° C. for 30 s of each cycle, followed by one cycle of 10 min at 72° C. A 0.8 kb PCR product containing truncated OSM amplicon was digested with NdeI and EcoRI enzymes and purified on agarose gel. The purified fragment was cloned into NdeI and EcoRI sites of pET20b vector (Novagen, Madison, Wis.) resulting pETOSM plasmid. The pETOSM15 clone was selected for further use after confirmation of nucleotide sequence.

Expression and purification of recombinant tobacco osmotin. The pETOSM 15 plasmid was introduced into *E. coli* Rosetta 2(DE3) pLysS strain (Novagen, Madison, Wis.), and the selected clone was cultured in LB medium containing 0.25% glucose, 10 mM MgSO4, 100 µg ampicillin ml$^{-1}$ and 50 µg chloramphenicol ml$^{-1}$ at 37° C. overnight. The overnight culture was used to inoculate in ZYM505 medium (1% tryptone, 0.5% yeast extract, 0.5% glycerol, 0.05% glucose, 50 mM NH$_4$Cl, 25 mM KH$_2$PO$_4$, 25 mM Na$_2$HPO$_4$, 5 mM Na$_2$SO$_4$, 0.05% glucose, 10 µM FeCl$_3$, 4 µM CaCl$_2$, 2.5 µM each of MnCl$_2$ and ZnSO$_4$, and 0.4 µM each of CoCl$_2$, CuSO$_4$, NiCl$_2$, Na$_2$MoO$_4$, Na$_2$SeO$_3$ and H$_3$BO$_3$) (Studier 2005) containing 50 µg ampicillin ml$^{-1}$ and 25 µg chloramphenicol ml$^{-1}$. The culture was grown at 37° C. and, at $OD_{650}$ of 1.5, was induced with 1 mM IPTG, and allowed to grow for 8 h at 37° C. The induced culture was adjusted to pH 7.0 with 10 M NaOH at 2, 4, and 6 h after initial induction. Cells were harvested by centrifugation at 4,500×g for 30 min, and sonicated in 50 mM Tris/HCl, 1 mM EDTA, pH 8.0. After removal of cell debris, lysed cells were centrifuged at 10,000×g for 10 min, and the inclusion bodies were collected as a pellet. The pellet was washed twice with 50 mM Tris/HCl, pH 8.0, and suspended in 10 mM Tris/HCl, pH 6.0 followed by addition of solid urea to a final concentration of 8 M to facilitate recovery of recombinant tobacco osmotin (rOSM) as soluble protein.

Soluble protein was mixed with CM-cellulose for 2 h in a 50 ml capped-tube with gentle shaking at 4° C. followed by centrifugation at 700×g for 5 min to remove unbound materials. The pellet was washed with five bed volumes of 8 M urea in 10 mM Tris/HCl, 1 mM EDTA at pH 7.5. The rOSM from CM-cellulose was eluted with one bed volume of 500 mM NaCl and 8 M urea in 50 mM Tris/HCl, pH 8.5 with gentle rotation for 12 h at 8° C. The protein eluted from CM-cellulose was collected as supernatant by centrifugation at 700×g for 5 min. To the eluted protein fraction, imidazole was added to a final concentration of 5 mM. The pH of the solution was adjusted to 7.0 and transferred onto cobalt (Co)-agarose affinity beads in a 50 ml capped conical tube and allowed to bind for 1 h at 4° C. with gentle shaking. The Co-agarose beads were washed twice with five bed volumes of washing buffer (8 M urea in 50 mM Tris/HCl, pH 7.0). The washed beads were collected by centrifugation at 700×g for 5 min. The rOSM was eluted with one column volume of 8 M urea and 100 mM imidazole in 50 mM Tris/HCl, pH 7.0 for 12 h at 8° C. The eluted protein was dialyzed for 24 h in 2 l 20 mM sodium acetate at pH 5.2. The purity of the recombinant rOSM was examined by SDS-PAGE and the protein content was measured by Bradford protein assay.

Antifungal assay of recombinant tobacco osmotin. Two yeast strains of human pathogens, *Candida albicans* (ATCC11651) and *Cryptococcus neoformans* (ATCC13690), and two non-pathogenic yeast strains, *Saccharomyces cerevisiae* (BWG7a from Purdue University) and *Pichia methanolica* (PMD11 from Invitrogen), were used to test the antifungal activity of rOSM. 100 µl of each overnight culture of the strains diluted with YPAD medium (1% yeast extract, 2% peptone, 2% glucose, 0.01% adenine) to OD650 of 0.02 was transferred into the wells of microplate. Twofold serial dilutions of rOSM ranging from 0 to 225 µg ml$^{-1}$ were added to each well. Final volume of each well was adjusted to 200 µl with YPAD medium. Plates were incubated at 30° C. for 48 h and the absorbance at OD650 of each well was recorded using a microplate reader. The YPAD medium with the same rOSM concentrations were used to calibrate the microplate reader. Relative growth of each culture was calculated as the absorbance of culture in the presence of rOSM divided by the absorbance of culture in YPAD medium without rOSM. The result was analyzed with SAS Version 9.2 for ANOVA and Tukey grouping for calculating the antimicrobial efficacy of rOSM.

Ferric (III) binding capacity of rOSM. To measure the ferric (III) ($Fe^{3+}$) binding capacity, rOSM was placed in dialysis tube (Spectrum™ Spectra/Por™ RC dialysis membranes, 6-8 kD molecular weight cut off, Rancho Dominguez, Calif.) and human heatshock protein 60 (HSD I) was used as a control for the possible binding of poly-histidine tag to iron. Samples were dialyzed 24 hrs in 2 ml of 10 mM and 1 mM $FeCl_3$ buffer with sodium or ammonium at pH 5.2 for rOSM binding to ions. Followed three changes with deionized water at 24 hrs a time for 4 days total, protein concentration was quantitated by comparing the intensity of rOSM to BSA control on SDS-PAGE gel stained with Coommassie blue. After 4 hr baking at 450° C., irons were dissolved in 25 ml of 1% hydrochloric acid for quantifying ions by atomic absorption analysis.

Results and Discussion

Earlier efforts to produce recombinant tobacco osmotin in bacterial cells were largely unsuccessful due to the toxicity and physical characteristics of this protein. An osmotin-like protein from *Solanum nigrum* (SnOLP) was expressed in *E. coli* using the T % promoter system (Campos Mde et al. 2008). Although these two proteins are similar, tobacco osmotin differs from SnOLP in some important surface amino acids that carry charges, particularly at the random coil which confers different surface properties (Min et al. 2004).

Expression of rOSM was optimal when the culture was induced at OD650 of 1.5 at pH 7.0. The pH of the culture medium was continuously adjusted during growth, otherwise the pH of the medium decreased to 5.5. The reasons for the drop in pH are not clear but may be related to the acidification of the medium resulting from the binding of iron to rOSM in *E. coli* cells and consequently increasing the importation of iron from the medium. Our unpublished results show that rOSM binds to $Fe^{3+}$ ions. Acidification of the medium occurs when *E. coli* cells grow, therefore, resulting in the uptake of iron and aluminum from a low buffering capacity medium (Guida et al. 1991). The ZYM505 medium has 50 mM phosphate buffer and 10 µM $FeCl_3$. Thus, removal of iron from the medium should not cause a dramatic pH change. Another unexplained observation is that the *E. coli* cells expressing rOSM lysed in hypotonic solutions (50 mM Tris/HCl, pH 8.0 and 1 mM EDTA), but not in the ZYM505 medium. Cells lysed during overnight growth in the modified ZYM505 medium lacking the iron or yeast extract. The pH of the medium in such cases increased to 8.0. These observations suggest that the rOSM play a role in the partitioning of cations in the ZYM505 medium resulting in its acidification. This hypothesis is supported by the fact that 40 mM NaOH was needed to maintain pH of iron-free ZYM505 medium (data not shown).

To minimize the toxicity to bacterial cells by rOSM, its expression was targeted through inclusion bodies (IB). The IB pellet was sticky and red in color. Table 1 summarizes the purification steps of rOSM.

TABLE 1

Summary of recovery and purification of rOSM

| Purification steps | Recovery of rOSM (%) | | Purity (%) |
|---|---|---|---|
| | Each step | Total | |
| *E. coli* culture[a] | 100 | 100 | 40 |
| Inclusion body | 95 | 95 | 80 |
| CM-cellulose[b] | 20 | 19 | 95 |
| Co-Agarose[c] | 20 | 3.8 | ~100 |

[a]Culture was induced at 1.5 $OD_{650}$ with IPTG at 37° C. for 8 h, and medium was maintained at pH 7.0. The rOSM was extracted from the inclusion body with 8M urea
[b]The urea soluble rOSM was purified by CM-cellulose, and eluted with 500 mM NaCl and 8M urea in 50 mM Tris/HCl. pH 8.5 for 12 h at 8° C.
[c]The CM-cellulose purified protein was applied to Cobalt (Co)-agarose affinity beads for further purification. The 8M urea and 100 mM imidazole in 50 mM Tris/HCl, pH 7.0 was used to elute the protein for 12 h at 8° C.. The eluted protein was dialyzed for 24 h in 2 l of 20 mM sodium acetate at pH 5.2

Figure 1:
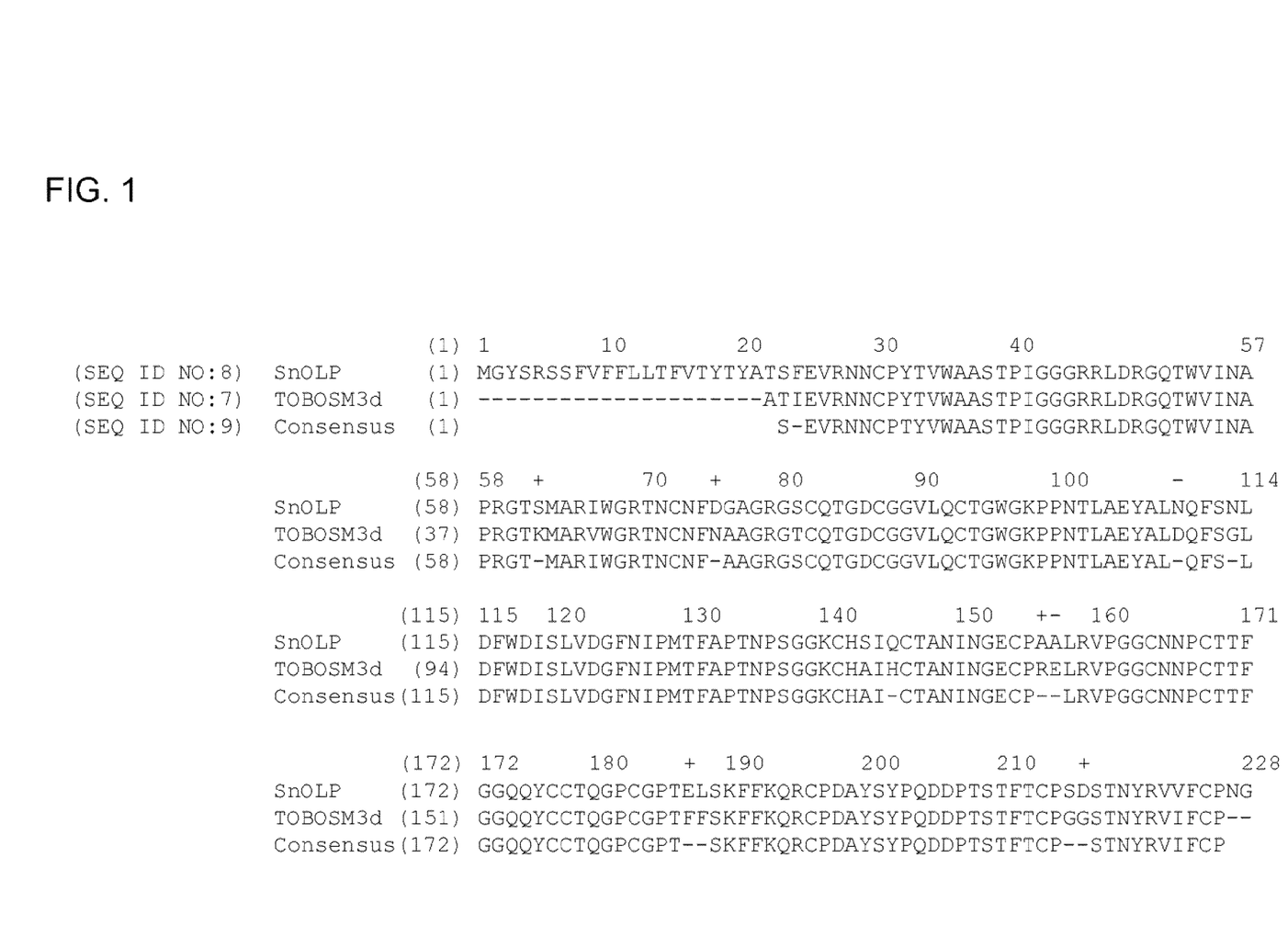
FIG. 1. Amino acid sequence alignment of tobacco osmotin (TOBOSM3d, sequence from IPCV.pdb) and *Solanum nigrum* osmotin like protein (SnOLP). Amino acid residues with charge difference are indicated with "+" or "−".
Figure 2:
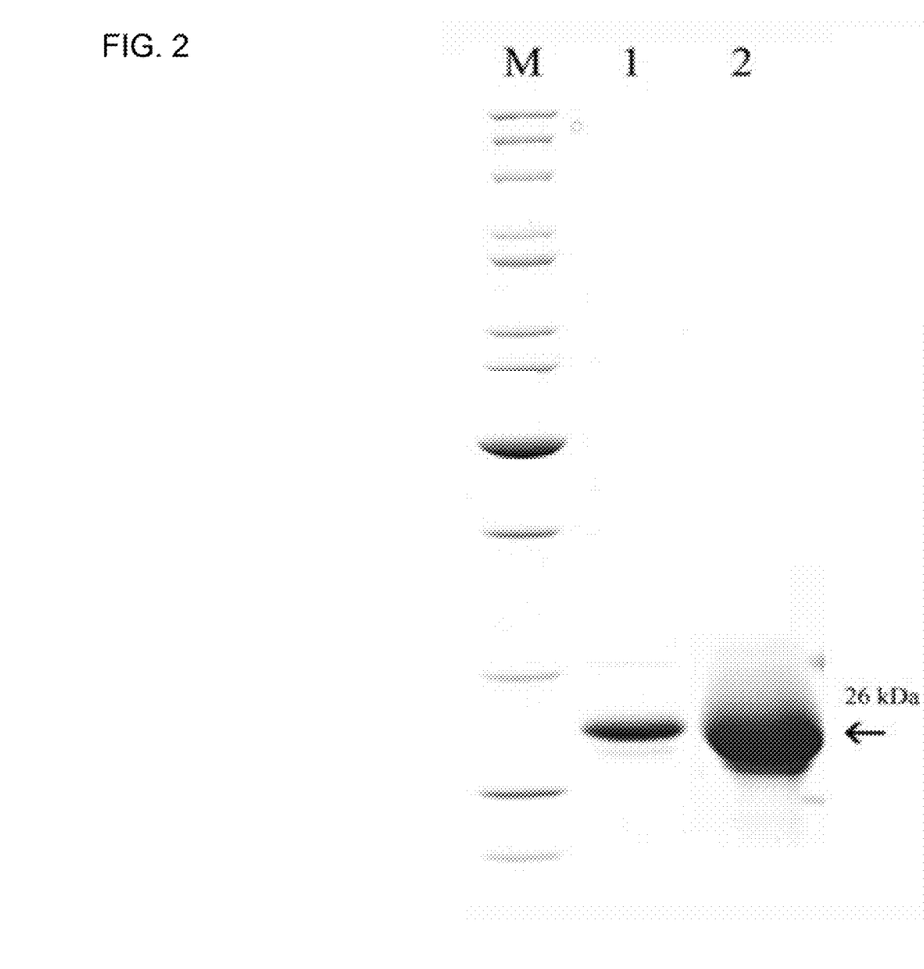
FIG. 2. SDS-PAGE of purified rOSM eluted from the Cobalt-agarose beads. Protein eluted from Cobalt-agarose beads were mixed with sample buffer, run on a 12% SDS-PAGE, and stained with Coomassie Blue R-250. Lane M shows molecular weight markers; lane 1 was loaded with 2 µg of rOSM, and lane 2 was loaded with 25 µg of rOSM. Note that lane 2 with overloaded purified rOSM did not show other protein bands.

The level of rOSM in the soluble protein from harvested cells was ~40%. The rOSM was extracted from the IB with 8 M urea. Approximately 95% of rOSM was recovered from IB with ~80% purity. The denatured urea soluble rOSM was subjected to CM-cellulose chromatography for further purification. Approximately 20% of the rOSM with 95% purity was recovered from CM-cellulose. The CM-cellulose eluant was applied to Co-agarose affinity beads in the presence of high purity urea. Approximately 20% of the applied rOSM was eluted from the Co-agarose beads with 100% purity (FIG. 1). A considerable loss of ~80% rOSM on both CM-cellulose and Co-agarose columns was observed. Starting with 2 l culture, the recovery of pure rOSM was between 40 and 50 mg with the protocol mentioned above. The recovery of rOSM was improved and the bound rOSM was further eluted when the elution process was repeated from both CM-cellulose and Co-agarose beads. After four repeated elutions, the final yield of rOSM was 200 mg from 2 l induced *E. coli* culture. The strong binding of rOSM to CM-cellulose and Co-agarose beads and its low elution may be due to the unique surface properties of rOSM. The existence of eight disulfide bonds in tobacco OSM (Singh et al. 1987) and the lower solubility (~0.6 mg ml$^{-1}$) of purified rOSM may contribute to this strong binding effect. Since rOSM is a stable protein, increased recovery by repeated elutions without loss of its bioactivity can be safely applied.

Both pathogenic and non-pathogenic strains of yeasts showed various degrees of growth inhibition by rOSM. The pathogenic yeast, *C. neoformans* exhibited highest inhibition of growth by rOSM with a MIC10 and MIC50 value of 0.44 and 14 µg ml$^{-1}$, respectively. Growth inhibition of *C. albicans* and *P. methonolica* required higher concentrations of rOSM (Table 2).

TABLE 2

Effect of rOSM on growth inhibition in yeast species

| Yeast species | $MIC_{10}$ (µg ml$^{-1}$)[a] | $MIC_{50}$ (µg ml$^{-1}$) |
|---|---|---|
| Candida albicans | 57 | 225 |
| Cryptococcus neoformans | 0.44 | 14 |
| Saccharomyces cerevisiae | 0.44 | 113 |
| Pichia methanolica | 28 | >225 |

[a]Aliquots of 100 µl of each overnight culture of the strains diluted with YPAD medium to $OD_{650}$ of 0.02 were transferred into the wells of the microplate. Twofold serial dilutions of rOSM ranging from 0 to 225 µg ml$^{-1}$ were added to each well. Final volume of each well was 200 µl. Plates were incubated at 30° C. for 48 h and the absorbance at $OD_{650}$ for each well was recorded. Minimum concentrations of rOSM to inhibit 10% of culture growth ($MIC_{10}$) and inhibit 50% of culture growth ($MIC_{50}$) are shown for each species of yeast Fungicidal activity of rOSM also was assayed on a solid medium according to the method used by Abad et al. (1996)

(data not shown). The growth inhibition test was comparable with the previous report of Yun et al. (1997) for *S. cerevisiae* strain BWG7. Native tobacco osmotin inhibited fungal growth probably by binding to the PHO36 receptor and cell wall glycoprotein causing cell apoptosis (Narsimhan et al. 2003, 2005) and growth inhibition (Yun et al. 1997, 1998; Narsimhan et al. 2003). It is likely that rOSM may have this dual mode in which it causes inhibition of yeast growth.

The rOSM bound to ferric (III) ions (Table 3).

TABLE 3

| | Binding condition | | | | |
|---|---|---|---|---|---|
| | | 1 mM Fe$^{3+}$/Na$^+$ | | 10 mM Fe$^{3+}$/Na$^+$ | 1 mM Fe$^{3+}$/NH$^{4+}$ |
| Proteins | HSD1 | OSM Supernatant | OSM precipitation | OSM supernatant | OSM supernatant |
| Fe$^{3+}$ bound/protein | 0.0087 | 0.191 | 0.257 | 0.104 | 0.003 |

Every Fe$^{3+}$ ion bound to 5 molecules of dissolved proteins or 4 precipitated OSM molecules tightly. This binding decreased if the concentration of iron increased, and totally was blocked by ammonium (Table 3). Although every OSM only bound ¼-⅕ Fe$^{3+}$ ions, the binding was very tight. Changing the buffer three times did not remove Fe$^{3+}$ (Table 3). Therefore, OSM has great potential not only for food safety control but also for medical therapies such as cancer prevention.

Example 2

Expression of Truncated Tobacco Osmotin in *Pichia methanolica*

Utilizing methods similar to those in Example 1, a truncated tobacco osmotin polypeptide was expressed in a *Pichia methanolica* system (Invitrogen). DNA encoding the truncated tobacco osmotin polypeptide was cloned into plasmid pMETA for cytosolic expression and pMETαA for secreted expression.

Confirmed yeast expression vectors, generated in *E. coli*, were linearized with compatible restriction endonucleases to separate the expression cassette from plasmids. Linearized plasmids were precipitated and purified by silica spin columns, and DNA concentrations were measured by absorbance ($\lambda$=260 nm). Three micrograms of these purified DNAs were incubated with *P. methanolica* competent cells prepared as recommendations of manufacturer. After incubation on ice for three minutes, competent cells were transferred to 2 mm gaped electroporation cuvettes, and a single pulse was applied with 750 v, 25 μF and a resistance setting of ∞Ω on a GenePulser (Bio-Rad). One milliliter of YPAD (1% yeast extract, 2% peptone, 2% glucose, 0.01% adenine) was added into each cuvette and transferred to a 2 ml microcentrifuge tube. After incubation at 30° C. for 1 hr without shaking, transformants were spun at 1,500×g for a minute and washed with 1 ml of 2× strength yeast nitrogen base (YNB, obtained from Invitrogen) to remove the excess adenine. The washed transformants were then collected with centrifugation and suspended with 100 μl of 2× strength YNB, and spread on 2 minimal dextrose agar plates (MDA, 2×YNB, 2% glucose, 40 ppm biotin, 1.5% agar) for ADE2 selection (Hiep et al. 1993 (a) and Hiep et al. 1993(b)). Single colonies were expected to be visible after 4 days of incubation at 30° C., and were further purified by streaked on another MDA plate.

To reduce the bias caused by somatic variations, two single colonies were picked from each MDA plate for small scale expression. Colonies were picked with wooden toothpicks and grown in 12 ml of Buffered Dextrose-complex Medium (BMDY, 1% yeast extract, 2% peptone, 100 mM potassium phosphate pH 6.0, 2×YNB, 4×10$^{-5}$% biotin, and 2% glucose) for 16-18 hrs at 30° C. with shaking. One milliliter of these overnight cultures was glycerol-stocked and the rest of the culture was used for induction by replacing the BMDY media with 4 ml of Buffered Methanol-complex Medium (BMDY, 1% yeast extract, 2% peptone, 100 mM potassium phosphate pH 6.0, 2×YNB, 4×10$^{-5}$% biotin, and 0.5% methanol) (Invitrogen, 2002). For every 24 hrs, additional 0.5% of methanol was fed to the culture, as well as, 1% soytone (Zhao et al 2008) at the first methanol feed, and 1% casamino at third feed to minimize the protease activities (Slininger et al. 2006, Hu et al. 2006, Rahbarizadeh et al. 2006). Twenty-four hours after the fourth methanol feed, the medium was harvested by centrifugation (Invitrogen, 2002). Medium and cells were collect separately.

Media protein and cellular protein were dissolved in SDS sample buffer and separated on a 12% Tris-glycine SDS polyacrylamide gel. After separation, the proteins were transferred to two PVDF membranes. Anti-osmotin IgY and anti-V5 tag mIgG were used for detecting expression via Western blotting. Truncated osmotin was detected intracellularly and in the culture media. Molecular weight analysis indicated that the alpha-mating factor had been processed and removed from the truncated osmotin. The expected yield is several hundred micrograms per one liter culture. No osmotin expression was observed in the pMETA clone.

REFERENCES

Abad L R, D'Urzo M P, Liu D, Narsimhan M L, Ruveni M, Zhu J K, Niu X, Singh N K, Hasegawa P M, Bressan R A (1996) Antifungal activity of tobacco osmotin has specificity and involves plasma membrane permeabilization. Plant Sci 118:11-23.

Campos Mde A, Silva M S, Magalhaes C P, Ribeiro S G, Sarto R P, Vieira E A, Grossi de Sa M F (2008) Expression in *Escherichia coli*, purification, refolding and antifungal activity of an osmotin from *Solanum nigrum*. Microb Cell Fact 7:7.

Fernandez V & Winkelmann G. 2005. The determination offerric iron in plants by HPLC using the microbial iron chelator desferrioxamine E. Biometals 18(1):53-62.

Hermes-Lima M, Ponka P & Schulman H M. 2000. The iron chelator pyridoxal isonicotinoyl hydrazone Guida L, Saidi Z, Hughes M N, Poole R K (1991) Aluminium toxicity and binding to *Escherichia coli*. Arch Microbiol 156:507-512.

Hiep et al. (1993a) Transformation in the methylotrophic yeast *Pichia methanolica* utilizing homologous ADE1 and heterologous *Saccharomyces cerevisiae* ADE2 and LEU2 genes as genetic markers. Yeast. November; 9(11): 1189-97.

Hiep et al. (1993b) The 5-aminoimidazole ribonucleotide-carboxylase structural gene of the methylotrophic yeast *Pichia methanolica*: cloning, sequencing and homology analysis. Yeast. November; 9(11):1251-8.

Hermes-Lima M, Ponka P & Schulman H M. 2000. The iron chelator pyridoxal isonicotinoyl hydrazone (PIH) and its analogues prevent damage to 2-deoxyribose mediated by ferric iron plus ascorbate. Biochim Biophys Acta 1523(2-3):154-160.

Hu et al. (2006) Codon optimization, expression, and characterization of an internalizing anti-ErbB2 single-chain antibody in *Pichia pastoris*. Protein Expr. Purif. May; 47(1):249-57.

Kononowicz A K, Nelson D E, Singh N K, Hasegawa P M & Bressan R A. 1992. Regulation of the Osmotin Gene Promoter. Plant Cell 4(5):513-524.

Liu D, Raghothama K G, Hasegawa P M, Bressan R A (1994) Osmotin overexpression in potato delays development of disease symptoms. Proc Natl Acad Sci USA 91:1888-1892.

Liu D, Rhodes D, D'Urzo M P, Xu Y, Narsimhan M L, Hasegawa P M, Bressan R A, Abad L (1996) In vivo and in vitro activity of truncated osmotin that is secreted into the extracellular matrix. Plant Sci 121:123-131.

Min K, Ha S C, Hasegawa P M, Bressan R A, Yun D J, Kim K K (2004) Crystal structure of osmotin, a plant antifungal protein. Proteins 54:170-173.

Narasimhan M L, Damsz B, Coca M A, Ibeas J I, Yun D J, Pardo J M, Hasegawa P M, Bressan R A (2001) A plant defense response effector induces microbial apoptosis. Mol Cell 8:921-930.

Narsimhan M L, Coca M A, Jin J, Yamauchi T, Ito Y, Kadowaki T, Kim K K, Pardo J M, Damsz B, Hasegawa P M, Yun D J, Bressan R A (2005) Osmotin is a homolog of mammalian adiponectin and controls apoptosis in yeast through a homolog of mammalian adiponectin receptor. Mol Cell 17:171-180.

Narsimhan M L, Lee H, Damsz B, Singh N K, Ibeas J J, Mastmuto T K, Woloshuk C P, Bressan R A (2003) Overexpression of a cell wall glycoprotein in *Fusarium oxysporum* increases virulence and resistance to a plant PR-5 protein. Plant J 36:390-400.

Rahbarizadeh et al., (2006) Overexpression of anti-MUC1 single-domain antibody fragments in the yeast *Pichia pastoris*. Mol. Immunol. February:43(5):426-35.

Singh N K, Handa A K, Hasegawa P M, Bressan R A (1985) Proteins associated with adaptation of cultured tobacco cells to NaCl. Plant Physiol 79:126-137.

Singh N K, Bracker C A, Hasegawa P M, Handa A K, Buckel S, Hermodson M A, Pfankoch E, Regnier F E, Bressan R A (1987) Characterization of osmotin: a thaumatin-like protein associated with osmotic adaptation in plant cells. Plant Physiol 85:529-536.

Singh N K, Nelson D E, Kuhn D, Hasegawa P M, Bressan R A (1989) Molecular cloning of osmotin and regulation of its expression by ABA and adaptation to low water potential. Plant Physiol 90:1096-1101.

Slininger et al. (2006) Nitrogen source and mineral optimization enhance D:-xylose conversion to ethanol by the yeast *Pichia stipitis* NRRL Y-7124. Appl. Microbiol. Biotechnol. October; 72(6): 1285-96.

Stintzi A, Heitz T S, Kauffmann S, Legrand M, Fritig B (1991) Thaumatin-like protein of virus-infected tobacco osmotin. Physiol Mol Plant Pathol 38:137-146.

Studier F W (2005) Protein production by auto-induction in high density shaking cultures. Protein Expr Purif 41:207-234.

Vigers A J, Weidmann S, Roberts W K, Legrand M, Selitrennikoff C P, Fritig B (1992) Thaumatin-like pathogenesis related proteins are antifungal. Plant Sci 83:155-161.

Woloshuk C P, Meulenhoff S J, Sela-Burlage M, Van den Eltzen P J M, Cornelissen B J C (1991) Pathogen-induced proteins with inhibitory activity toward *Phytophthora infestans*. Plant Cell 3:619-628.

Yun D J, Zhao Y, Pardo J M, Narasimhan M L, Damsz B, Lee H, Abad L R, D'Urzo M P, Hasegawa P M, Bressan R A (1997) Stress proteins on the yeast cell surface determine resistance to osmotin, a plant antifungal protein. Proc Natl Acad Sci USA 94:7082-7087.

Yun D J, Ibeas J I, Lee H, Coca M A, Narsimhan M L, Uesono Y, Hasegawa P M, Pardo J M, Bressan R A (1998) Osmotin, a plant antifungal protein, subverts signal transduction to enhance fungal cell susceptibility. Mol Cell 1:807-817.

Zhao et al. (2008) Increasing the cell viability and heterologous protein expression of *Pichia pastoris* mutant deficient in PMR1 gene by culture condition optimization November; 81(2):235-41.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

The invention claimed is:

1. A method for producing a recombinant tobacco osmotin polypeptide, the method comprising:
(a) growing in culture media microbial host cells transformed with a vector that inducibly expresses the tobacco osmotin polypeptide, wherein the culture media comprises about 2-20 µM $Fe^{3+}$;
(b) inducing expression of the tobacco osmotin polypeptide;
(c) adjusting pH of the culture media to about 6.5-7.5 after inducing expression of the tobacco osmotin polypeptide; and
(d) isolating the tobacco osmotin polypeptide, wherein at least about 50 mg tobacco osmotin polypeptide per liter of culture media is isolated.

2. The method of claim 1, wherein the pH of the culture media is adjusted upward after inducing expression of the tobacco osmotin polypeptide.

3. The method of claim 2 comprising adjusting the pH of the culture a first time to about 6.5-7.5 at about 1-3 hours after inducing expression of the tobacco osmotin polypeptide, and then adjusting the pH of the culture media a second time to about 6.5-7.5 at about 3-5 hours after inducing expression of the tobacco osmotin polypeptide, and then adjusting the pH of the culture a third time to about 6.5-7.5 at about 5-7 hours after inducing expression of the tobacco osmotin polypeptide.

4. The method of claim 1, wherein the pH of the culture is adjusted continuously after inducing expression of the tobacco osmotin polypeptide.

5. The method of claim 1, wherein expression of the tobacco osmotin polypeptide is induced by adding isopropyl β-D-1-thiogalactopyranoside to the culture media when the culture media has an $OD_{650}$ of between about 1-2.

6. The method of claim 1, wherein expression of the tobacco osmotin polypeptide is induced indirectly by adding isopropyl β-D-1-thiogalactopyranoside to the culture media.

7. The method of claim 1, wherein the culture media comprises about 2-20 µM $FeCl_3$.

8. The method of claim 1, wherein the vector expresses a tobacco osmotin polypeptide comprising SEQ ID NO:5 or a variant thereof having at least 95% amino acid sequence identity to SEQ ID NO:5 and exhibiting one or more functional activities of tobacco osmotin.

9. The method of claim 1, wherein the tobacco osmotin polypeptide produced by the method has anti-fungal activity and inhibits growth of a culture of one or more yeast species selected from a group consisting of *Candida albicans, Cryptococcus neoformans, Sacccharomyces cerevisiase,* and *Pichia methanolica.*

10. The method of claim 9, wherein the tobacco osmotin polypeptide inhibits 50% of growth of the culture when the tobacco osmotin polypeptide is present in the culture at a concentration of no more than about 300 µg/ml.

11. The method of claim 9, wherein the tobacco osmotin polypeptide inhibits 10% of growth of the culture when the tobacco osmotin polypeptide is present in the culture at a concentration of no more than about 100 µg/ml.

12. The method of claim 1, wherein the microbial host cells are bacteria.

13. The method of claim 12, wherein the bacteria is *E. coli.*

14. The method of claim 13, wherein the *E. coli* inducibly expresses T7 RNA polymerase in the presence of IPTG and the vector expresses the tobacco osmotin polypeptide in the presence of T7 RNA polymerase.

15. The method of claim 13, wherein the tobacco osmotin polypeptide is expressed in inclusion bodies of the *E. coli* and the tobacco osmotin polypeptide is isolated via isolating the inclusion bodies and solubilizing the tobacco osmotin polypeptide in the inclusion bodies.

* * * * *